United States Patent [19]

Colle et al.

[11] Patent Number: 4,766,139

[45] Date of Patent: Aug. 23, 1988

[54] TRIAZOLYL-KETO-DERIVATIVES HAVING FUNGICIDE ACTIVITY

[75] Inventors: Roberto Colle, Basiglio; Franco Gozzo, S. Donato Milanese; Giovanni Camaggi, Lodi; Luigi Mirenna, Milan; Angela Zagni, Peschiera Borromeo, all of Italy

[73] Assignee: Montedison S.p.A., Milan, Italy

[21] Appl. No.: 722,009

[22] Filed: Apr. 11, 1985

[30] Foreign Application Priority Data

Apr. 11, 1984 [IT] Italy ............................. 20484 A/85

[51] Int. Cl.$^4$ .................... C07D 248/08; A01N 43/50
[52] U.S. Cl. ..................................... 514/383; 548/262
[58] Field of Search ................ 548/262, 341; 514/383, 514/399

[56] References Cited

U.S. PATENT DOCUMENTS 4,291,044 9/1981 Jager .................................. 548/262

FOREIGN PATENT DOCUMENTS

| 896914 | 6/1983 | Belgium | 548/262 |
| 0079856 | 5/1983 | European Pat. Off. | 514/383 |
| 0149235 | 7/1985 | European Pat. Off. | 548/262 |
| 2847050 | 5/1980 | Fed. Rep. of Germany | 514/383 |
| 2121042 | 2/1986 | United Kingdom | 548/262 |

Primary Examiner—Glennon H. Hollrah
Assistant Examiner—Patricia L. Morris

Attorney, Agent, or Firm—Stephens, Davis, Miller & Mosher

[57] ABSTRACT

There are disclosed compounds having the formula (I) and (II):

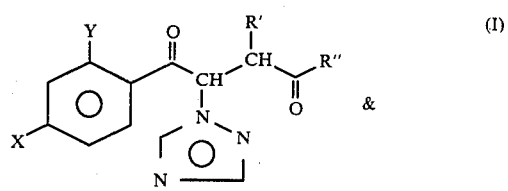

(I)

&

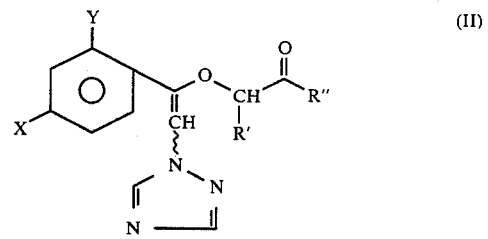

(II)

wherein:
R' and R", equal to or different from each other, are a $C_1$-$C_7$ alkyl, a $C_3$-$C_7$ cycloalkyl, a heterocycloalkyl, alkoxyalkyl, dialkoxyalkyl, haloalkyl;
X is a halogen, a $C_1$-$C_4$ alkyl, a haloalkyl, alkoxyl, phenyl; and
Y is H or a halogen.

9 Claims, No Drawings

TRIAZOLYL-KETO-DERIVATIVES HAVING FUNGICIDE ACTIVITY

The present invention relates to new triazolyl-keto-derivatives, existing in several isomeric forms, to a method for preparing said compounds and to the respective use of same in the agriculture.

BE-PS No. 896 914 in the name of Montedison S. p. A. discloses a new class of triazolyl-keto-derivatives, having funicide activity and characterized by the following general formula:

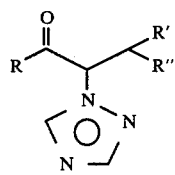

wherein
R is an alkyl, alkenyl, phenyl group, optionally substituted;
R" is an alkoxycarbonyl, alkylcarbonyl, arylcarbonyl, aminocarbonyl, cyano group;
R' has the same meanings as R and R".

Now we have found two series of compounds, one of which is characterized by a general formula comprised by the formula of the aforesaid Belgian patent and which are endowed with a wide range of fungicide activity and, surprisingly, with systemic properties.

The object of the present invention are compounds having the following general formulae (I) and (II)

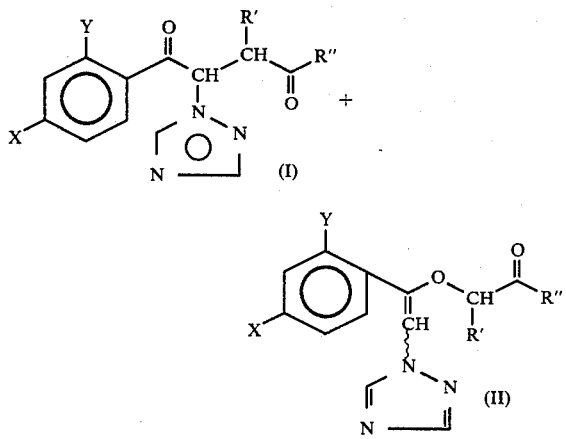

wherein:
R' and R", equal to or different from each other, are: a linear or branched $C_1$-$C_7$ alkyl group; a $C_3$-$C_7$ cycloalkyl group, optionally substituted by $C_1$-$C_4$ alkyl groups; a heterocycloalkyl group; an alkoxyalkyl group having from 1 to 4 carbon atoms both in the alkylic and in the alkoxylic part; a dialkoxyalkyl group having from 1 to 4 carbon atoms both in the alkylic and in the alkoxylic part or a $C_1$-$C_4$ haloalkyl group;
X is a halogen atom, preferably Cl and F; a $C_1$-$C_4$ alkyl group; a $C_1$-$C_4$ haloalkyl group; a $C_1$-$C_4$ alkoxy group; or a phenyl group;
Y is H or a halogen atom, preferably Cl and F.

The synthesis processes of the compounds of formula (I) and (II) consist in reacting in an inert solvent, a compound of the formula:

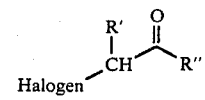

(wherein R' and R" have the above meanings and halogen=Cl, Br) with a sodium salt of an aryltriazolylketone, according to the reaction:

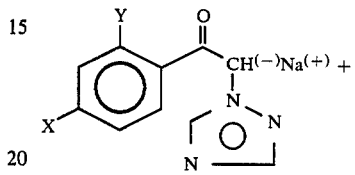

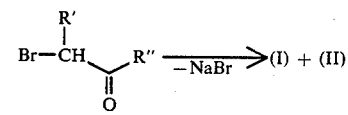

According to the above process one generally obtains mixtures of compounds of formulae (I) and (II). The ratio between compounds of formula (I) and compounds of formula (II), present in the reaction mixture, depends on the nature of the substituents R' and R", independently from the reaction conditions.

In particular, when R' is different from hydrogen, the amount of the compounds of formula (II) (0-alkylation) increases by increasing of the steric hindrance of radical R" for example: when R' is methyl and R" is tert.-butyl, one obtains prevailingly compounds of formula (II).

On the contrary when R' is hydrogen, prevailingly compounds of formula (I) are obtained independently of the meaning of radical R". From the reaction mixture it is possible to separate the single isomers of (I) and (II) by conventional methods.

Furthermore, it has been found, and this forms another object of the present invention, that the compound of formula (I) and the geometrical isomers E Z of compounds of formula (II), may be changed one into the other, by means of irradiation by U.V. light.

Examples of compounds prepared according to the present invention are set forth in Table 1 (the symbol Tr represents 1,2,4-triazol-1-yl radical), whereas the corresponding spectroscopic data are set forth in Tables 1A and 1B.

TABLE 1

| Compound No | Isomeric forms | Structure | m.p. °C. |
|---|---|---|---|
| 1 a + b | (I) + (II Z) | [structure shown] | oil |

TABLE 1-continued

| Compound No | Isomeric forms | Structure | m.p. °C. |
|---|---|---|---|
| 1 b | (II Z) | [structure] | 112-113 |
| 2 a + b | (I) + (II Z) | [structures] | oil |
| 3 b | (II Z) | [structure] | oil |
| 3 a | (I) | [structure] | oil |
| 4 a + b | (I) + (II Z) | [structures] | oil |
| 4 a | (I) | [structure] | 119-122 |
| 4 b | (II Z) | [structure] | 74-76 |
| 5 | (I) | [structure] | 123-124 |
| 6 b | (II Z) | [structure] | 112-113 |
| 6 a | (I) | [structure] | 145-147 |
| 6 c | (II E) | [structure] | 72-74 |
| 7 | (II Z) | [structure] | 98-100 |
| 8 | (II Z) | [structure] | oil |
| 9 | (II Z) | [structure] | 105-106 |

TABLE 1A

| N° Compound | −¹H.N.M.R. Spectra |
|---|---|
| 1 a + b (I + II Z) | δ 9.1(s, 1H), 8.3(s, 1H), 7(s, 1H), 7.85-7.2 (m, 8H), 6.7(s, 1H), 6.2(d, 1H), 4.5(q, 1H), 3.4(dp, 1H), 2.4(s, 3H), 2.1(s, 3H), 1.3(d, 3H), 0.9(d, 3H). |
| 1 b (II Z) | δ 9.1(s, 1H), 8(s, 1H), 7.3(m, 4H), 6.7(s, 1H), 4.5(q, 1H), 2.1(s, 3H), 1.3(d, 3H). |
| 2 a + b (I + II Z) | δ 9.15(s, 1H), 8.3(s, 1H), 8(s, 1H), 7.8(s, 1H), 8-7.4(m, 8H), 6.7(s, 1H), 6.2(d, 1H), 4.4(t, 1H), 3.8(dt, 1H), 2.4(s, 1H), 2.1(s, 1H), 1(t, 6H). |
| 3 b (II Z) | δ 9.15(s, 1H), 8.05(s, 1H), 7.45(m, 4H), 6.67 (s, 1H), 4.4(t, 1H), 2(s, 3H), 2-1(m, 6H), 0.9(t, 3H). |
| 3 a (I) | δ 8.3(s, 1H), 7.95(s, 1H), 8-7.21(m, 4H), 6.3 (d, 1H), 3.8(dt, 1H), 2.1(s, 3H), 2.1-1 (m, 6H), 0.9(t, 3H). |
| 4 a + b (I + II Z) | δ 8.35(s, 1H), 8.3(s, 1H), 7.95(s, 1H), 7.9 (s, 1H), 8-7.21(m, 4H), 6.3(d, 1H), 6.2(d, 1H), 3.8(dt, 1H), 3.7(dq, 1H), 2.7(q, 2H), 2.1(s, 3H), 2.1-1(m, 6H), 1.1(d, 3H), 1(t, 3H), 0.9(t 3H). |
| 4 a (I) | δ 8.35(s, 1H), 7.9(s, 1H), 7.85-7.2(m, 4H), 6.2(d, 1H), 3.7(dq, 1H), 2.7(q, 2H), 1.1(d, 3H), 1(t, 3H). |
| 4 b (II Z) | δ 9.2(s, 1H), 8(s, 1H), 7.45(m, 4H), 6.8 (s, 1H), 4.5(q, 1H), 2.3(q, 2H), 1.4(d, 3H), 1(t, 3H), |
| 5 (I) | δ 8.32(s, 1H), 7.7(s, 1H), 7.85-7.2(m, 4H), 6.3(d, 1H), 3.7(dt, 1H), 2.65(t, 2H), 1.8-1.2 (m, 4H), 0.95(t, 6H). |
| 6 b (II Z) | δ 9.44(s, 1H), 8(s, 1H), 7.4(m, 4H), 6.76(s, 1H), 5.05(q, 1H), 1.42(d, 3H), 0.96(s, 9H). |
| 6 a (I) | δ 8.2(s, 1H), 7.85(s, 1H), 7.78-7.3(m, 4H), 6.1(d, 1H), 4.05(dq, 1H), 1.18(s, 9H), 0.88 (d, 3H). |
| 6 c (II E) | δ 9.75(s, 1H), 7.6(s, 1H), 7.18(m, 4H), 6.4 (s, 1H), 5.05(q, 1H), 1.5(d, 3H), 1.2(s, 9H). |
| 7 (II Z) | δ 9.5(s, 1H), 8(s, 1H), 7.3(m, 4H), 6.75(s, 1H), 5.05(q, 1H), 1.5(d, 3H), 1(s, 9H). |

TABLE 1A-continued

| N° Compound | −¹H.N.M.R. Spectra |
|---|---|
| 8 (II Z) | δ 9.2(s, 1H), 7.8(s, 1H), 7.2(m, 4H), 6.75 (s, 1H), 4.7(q, 1H), 1.5(d, 3H), 1(s, 9H). |
| 9 (II Z) | δ 9.45(s, 1H), 8(s, 1H), 7.4(m, 4H), 6.7(s, 1H), 5.1(t, 1H), 3.7(d, 2H), 3.35(s, 3H), 0.95(s, 9H). |

TABLE 1B

| Compound No | Spectra I.R. Absorption bands, cm⁻¹ (ν C = O, ν = O) |
|---|---|
| 1 a + b (I + II Z) | 1710, 1700 |
| 1 b (II Z) | 1728, 1670 |
| 2 a + b (I + II Z) | 1725, 1690 |
| 3 b (II Z) | 1695 |
| 3 a (I) | 1725, 1700 |
| 4 a + b (I + II Z) | 1725, 1705 |
| 4 a (I) | 1705, 1690 |
| 4 b (II Z) | 1725, 1665 |
| 5 (I) | 1700 |
| 6 b (II Z) | 1720, 1698 |
| 6 a (I) | 1700, 1685 |
| 6 c (II Z) | 1712, 1645 |
| 7 (II Z) | 1720, 1675 |
| 8 (II Z) | 1715, 1680 |
| 9 (II Z) | 1705, 1670 |

Other representative examples of compounds falling under formula (I) of the present invention are set forth herebelow (the symbol "Tr" represents 1,2,4-triazol-1-yl radical and the symbol "Ar" represents a phenyl group containing the substituents indicated in formula (I)):

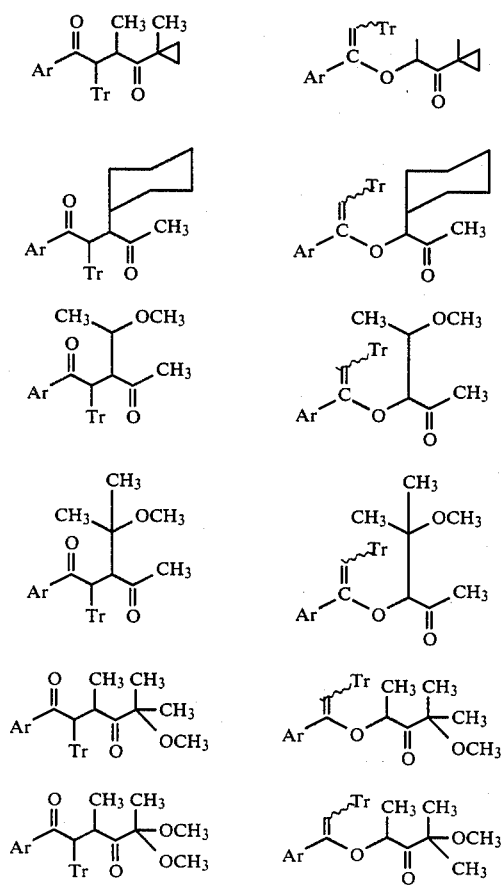
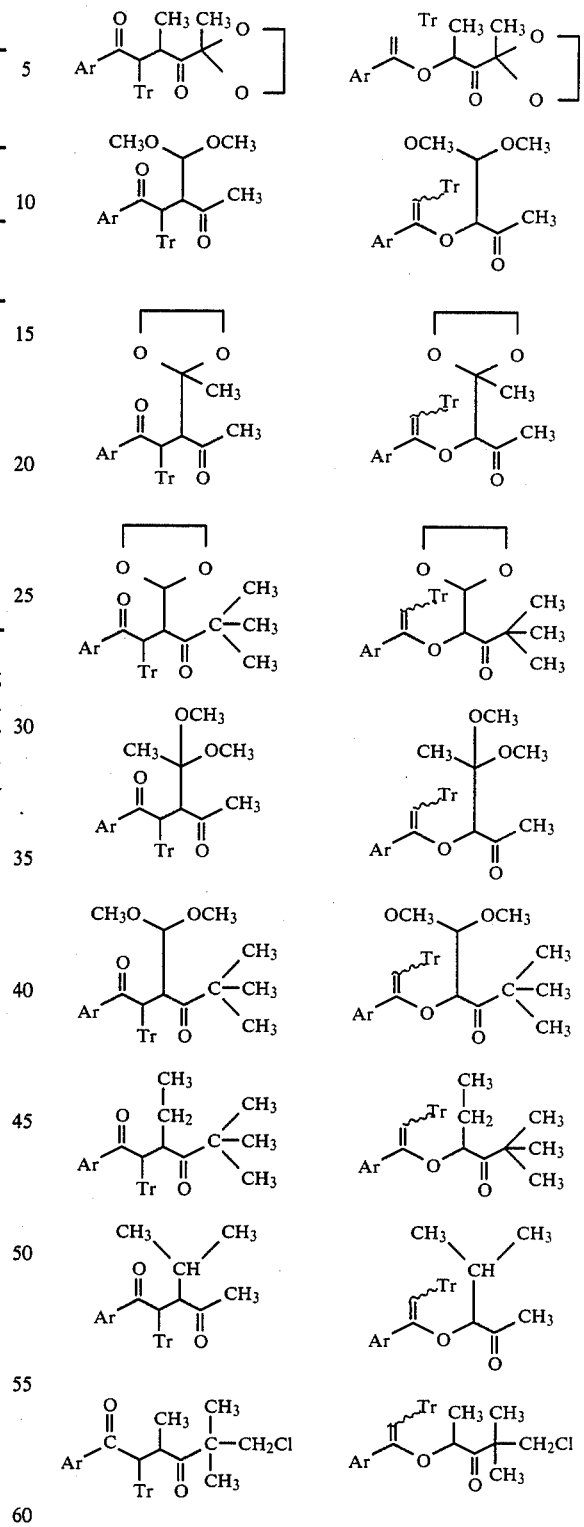

The compound of formulae (I) and (II) in the different isomeric forms wherein they have been obtained according to the present invention are endowed with high fungicide systemic activity, which permits the use in agriculture for protecting the useful plants from the action of phytopathogenous fungi.

A further object of the present invention is the use of the compounds of formulae (I) and (II) as systemic fungicides in fields and compositions that control these compounds as an active ingredient.

In particular the compounds of formula (I) and (II) are endowed with a particularly high fungicide activity against phytopathogenous fungi infecting the growing of cereals, curcurbitaceae, vine and fruit trees. Examples of plant diseases which can be fought by means of the compounds of the present invention are the following:

*Erysiphe graminis* on cereals, *Spherotheca fuliginea* on cucurbitaceae (for instance cucumber), Pucccinia on cereals, Septoria on cereals, Helminthosporium on cereals, Rhynchosporium on cereals, *Podosphaera leucotricha* on apple-trees, *Uncinula necator* on vines, *Venturia inequalis* on apple-trees, *Plasmopara viticola* on vines, *Pericularia oryzae* on rice, *Botrytis cinerea* on tomatoes, vines, strawberries, *Phytophthora infestans* on tomatoes, Fusarium on cereals, and still other diseases.

Furthermore the compounds of formula (I) and (II) possess other positive characteristics, such as a fungicide action having both preventive and curative character and a complete compatibility with the plants to be protected against fungus infection. Though the high fungicide activity with preventive and curative application is a common characteristic for all the terms of the series of formula (I) and (II), very considerable variations in the activity degree have been pointed out in the applications based on the penetration and translation of the compounds into the plant. These latter applications, such as for instance, the supply and absorption through the roots, depend in a determinant way, besides on the intrinsic activities, on the systemic properties of the products. These, in fact, must enter the vascular systems of the plants to act in places (for instance leaves) that are very far away from the ones they are applied in (for instance roots).

The systemic properties are affected in a determinant way by the isomery, so that in a few structures R', R'', X and Y being equal, only one of the two isomeric forms of compounds (I) and (II) is active, when the compound is supplied to the soil and taken up through the roots.

According to our own present knowledges we cannot individualize a rule to assign the systemic properties to a particular isomer. In fact, as it turns out from the data of biologic activity set forth in Table 2, in a few cases these properties are connected with the regio isomer of type (II) (examples of such cases are the compounds No.6b and 6c in comparison with 6a, whereas in other cases the same properties are connected with the regio isomer of type (I) and they are absent in the isomer of type (II) (for instance, compare compounds No. 4a and 4b).

We deem it interesting to point out that, on account of the properties discovered in the different isomer forms, the compounds of formula (I) and (II) may exist in, in the pure state or in mixtures, said compounds can be used for protecting the plants against the fungus infections with performances higher than the ones of the Prior Art according to the cited Belgian patent.

For practical uses in agriculture it is often useful to have available fungicide compositions containing one or more compounds of formula (I) and (II) as active substance.

The application of these compositions can take place on every part of the plants for instance: leaves, stalks, branches and roots, or on the seeds themselves before sowing, or in the soil where the plant grows as well. Compositions can be used, which are in the form of dry powers, wettable powers, emulsifiable concentrates, pastes, granulates, solutions, suspensions etc.: the choice of the composition kind will depend on the specific employ. The compositions are prepared according to the known technique, for instance, by diluting or dissolving the active substance by means of a solvent medium and/or a solid diluent, optionally in the presence of surfactants. As solid diluents or carriers, use may be made of: silica, kaolin, bentonite, talc, diatomite, dolomite, calcium carbonate, magnesia, gypsum, clays, synthetic silicates, attapulgite, sepiolite. As liquid diluents, besides, of course, water, use may be made of various types of solvents, for instance aromatic solvents (benzene, xylene, or mixtures of alkylbenzenes), chloroaromatic solvents (chlorobenzene), paraffins (oil fractions), alcohols (methanol, propanol, butanol), amines, amides (dimethylformamide), ketones (cyclohexanone, acetophenone, isophorone, ethylamylketone), esters (isobutyl acetate). As surfactants: sodium salts, calcium salts, triethanolamine salts of alkylsulfates, alkylsulfonates, alkylarylsulfonates, polyethoxylated alkylphenols, fatty alcohols condensed with ethylene oxide, polyethoxylated fatty acids, polyethoxylated sorbitol and sorbitan esters, polyethoxylated fats, ligninsulfonates. The compositions may also contain special additives for particular purposes, for instance adhesion agents such as gum-arabic, polyvinyl alcohol, polyvinylpyrrolidone.

If desired, it is possible to add to the compositions object of the present invention other compatible active substances as well, such as fungicides, phytodrugs, phytogrowth regulators, herbicides, insecticides, fertilizers.

The concentration of active substance in the aforesaid composition can vary within a wide range, depending on the active compound, the cultivation, the pathogen, environmental conditions and the kind of formulation that has been used. Generally the concentration ranges from 0.1 to 95, preferably from 0.5 to 90% by weight.

The following examples will illustrate the invention.

EXAMPLE 1

Preparation of

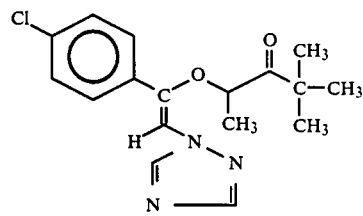

(Z)-1-(1-trimethylacetylethyl)oxy-1-(4-chlorophenyl)-2-(1-triazolyl)ethene—Compound 6b (II Z)

4 g of 1-(4-chlorophenyl)-2-(1-triazolyl)ethanone (0.018 moles) in 20 ml of DMF were added drop by drop and under a nitrogen atmosphere to a suspension of 0.866 g of sodium hydride in oil at 50% (0.018 moles) in anhydrous DMF (20 ml) at 0° C.

The mixture was kept under stirring for at least 30' at room temperature, thereby obtaining a limpid dark-red coloured solution of the sodium salt of triazolylketone. This solution was poured drop by drop, always under nitrogen atmosphere, into a solution of 3.47 g of 2-bromo-4,4-dimethyl pentane-3-one (prepared according to Colonge Grenat; Bull. Soc. Chim. 1.304 (1954)) in 20 ml of anhydrous DMF, keeping the temperature between 5° and 10° C.

After 8 hours, under stirring, at room temperature, the reation mixutre was poured into 500 ml of H₂O, and the formed precipitate was filtered, washed with plenty of water, dried in the air and crystallized from isopropyl alcohol. Thus one obtained 3 g of a crystalline white product having a melting point of 112°–113° C., which, on the ground of IR, NMR data (see Table 1) correspond to the above structure.

EXAMPLE 2

Isomerization reaction of compound 6b (II Z) (obtained according to Example 1) through irradiation by means of U.V. light.

2 g of compound 6b (II Z) of Example 1 were dissolved in 100 ml of methylene chloride and irradiated for 12 hours by means of a tungsten lamp Osram-Sonne Ultra-Vitalux 300 W.

The reaction mixture was separated on chromatographic column (eluent ether-n-hexane 1:2).

3 fractions were obtained, which on the ground of the spectroscopic data (see Table 1A and 1B) had been characterized as follows:

fraction I (RF greater, 100 mg): unchanged starting compound fraction II (50 mg): compound 6a (I) (see Table 1) m.p. 145°–7° C. (n-hexane)

fraction III (RF smaller, 1 g): compound 6c (II E) (see Table 1) with m.p. 72°–74° C. (n-hexane)

EXAMPLE 3

Isomerization reaction of compound No. 6b (II Z) (obtained according to Example 1), through irradiation by means of U.V. light on thin layer.

2 g of compound 6b (II Z) of Example 1 were dissolved in 50 ml of methylene chloride.

The resulting solution was spread uniformly on a glass sheet of 0.5 m² and irradiated for 12 hours by means of a tungsten lamp Osram Sonne Ultra Vitalux ®300 W. After irradiation the solid layer was dissolved in methylene chloride and after removal of the solvent it was subjected to column chromatography (eluent ether-hexane 1:2).

2 main fractions were obtained: the first one (RF greater) corresponded to starting compound unchanged (1.2 g). The second one corresponded to 400 mg of compound 6a (I). The compound 6c (II E) was present only in slight traces in the reaction mixture.

EXAMPLE 4

Preparation and separation of the reaction mixtures containing two isomer compounds 1-(4-chlorophenyl)-2-(1-triazolyl)-3-methylhexane-1,4-dione [compound 4a (I)] and (Z)-1-(1-propionylethyl)oxy-1-(4-chlorophenyl)-2-(1-triazolyl)ethene (compound 4b (II Z)

By treating 3.7 g (0.0226 moles) of 2-bromopentane-3-one with 0.0226 moles of sodium salt of 4-chlorophenyl-2-(1-triazolyl)-ethanone (obtained, in its turn, from 5 g of triazolyl derivative and 1.08 g of sodium hydride at 50% in DMF), after working as in example 1, a raw product was obtained, which at ¹H NMR analysis appeared as an equimolecular mixture of the two isomers (I) and (II) (see Table NMR). This mixture was subjected to column chromatography using hexane-ethyl acetate in a ratio ranging from 7:3 to 1:1. 2 unitary fractions were obtained consisting of 1.5 g of compound 4b (II Z) (RF greater) as a white solid (m.p. 74°–76° C.—isopropyl ether) and 1 g of compound No. 4a (I) which crystallized from petroleum ether in a crystalline white solid (0.7 g) at m.p. 119°–122° C. IR and NMR were consistent with the structures assigned to the two isomers.

EXAMPLE 5

Determination of the fungicide activity against cucumber oidium [*Sphaeroteca fuligenea* (Schlech) Salmon].

Preventive activity:

Cucumber plants c.v. Marketer, grown in pot in a conditioned environment, were sprayed on the lower leaf face with the products under examination in a water-acetone solution containing 20% of acetone (vol./vol.). Then the plants were kept in a conditioned environment for 6 days and at the seventh day they were sprayed on the upper leaf face with an aqueous suspension of conidia of *Sphaerotheca fuliginea* (200.000 conidia per ml). The plants were then carried back into a conditioned environment.

At the end of the incubation period of the fungus (8 days), the infection degree was evaluated by means of indexes of a valuation scale ranging from 100 (=sound plant) to 0 (=completely infected plant).

Curative activity:

Cucumber plants c.v. Marketer, grown in pot in a conditioned environment, were sprayed on the upper leaf face with an aqueous suspension of conidia of *Sphaerotheca fuliginea* (200.000 conidia ml). After 24 hours from the infection the plants were treated with the products under examination in a water-acetone solution containing 20% of acetone (vol./vol.), by spraying both leaf faces.

At the end of the incubation period of the fungus (8 days), during which time the plants were kept in a suitably conditioned environment, the infection degree was evaluated by means of indexes of a valuation scale ranging from 100 (=sound plant) to 0 (=completely infected plant).

Systemic activity by treatment through the roots:

Cucumber plants c.v. Marketer, grown in pot in a conditioned environment were treated by addition to the soil of an aqueous dispersion of the products under examination. After 24 hours the leaves were sprayed on the upper face, with an aqueous suspension of *Sphaerotheca fuliginea* (200.000 conidia per cc).

At the end of the incubation period (8 days) the infection degree was evaluated at sight by means of indexes of a valuation scale ranging from 100 (=sound plant) to 0 (completely infected plant).

The results are set forth in Table 2 in comparison with a compound of BE-PS 896 914.

EXAMPLE 6

Determination of the fungicide activity against wheat oidium (*Erysiphe graminis* D.C.).

Preventive activity:

The leaves of wheat c.v. Irnerio, grown in pot in a conditioned environment, were treated by spraying both faces with the products under examination in a water-acetone solution containing 20% of acetone (vol./vol.).

After a stay period of 1 day in conditioned environment at 20° C. and at 70% relative humidity, the plants were sprayed on both leaf faces with an aqueous suspension of *Erysiphe graminis* (200.000 conidia per ml). After a stay period of 24 hours in a room saturated with moisture, at 21° C., the plants were kept in a conditioned environment for the fungus incubation.

At the end of said period of time (12 days), the infection degree was evaluated at sight, by means of indexes of a valuation scale ranging from 100 (=sound plant) to 0 (completely infected plant).

Curative activity:

The leaves of wheat cv. Irnerio, growth in pot in a conditioned environment were sprayed on both leaf faces with an aqueous suspension of *Erysiphe graminis* (200.000 conidia per ml). After a stay period of 24 hours in a room saturated with moisture, at 21° C., the leaves were treated with the products under examinations in a water-acetone solution containing 20% of acetone (vol./vol.) by spraying both leaf faces. At the end of the incubation period (12 days), the infection degree was evaluated at sight, by means of indexes of a valuation scale ranging from 100 (=sound plant) to 0 (=completely infected plant).

The results are set forth in Table 2 in comparison with a compound of the Belgian patent.

EXAMPLE 7

Determination of the fungicide activity against the wheat linear rust (*Puccinia graminis* pers.).

Preventive activity:

The leaves of wheat cv. Irnerio, grown in pot in a conditioned environment, were treated by spraying both leaf faces with the products under examination in a water-acetone solution containing 20% of acetone (vol./vol.). After a stay period of 1 day in a conditioned room at 23° C. and 70% relative humidity, the plants were sprayed on both leaf faces with a spore mixture of *Puccinia graminis* in talc (100 mg of spores/5 g of talc).

After a stay period of 48 hours in a room saturated with moisture, at 21° C., the plants were kept in a conditioned environment for the fungus incubation.

At the end of said period (14 days), the infection degree was evaluated at sight, by means of indexes of a scale ranging from 100 (sound plant) to 0 (completely infected plant).

Curative activity:

The leaves of wheat cv. Irnerio, grown in pot in a conditioned environment, were sprayed on both leaf faces with a spore mixture of *Puccinia graminis* in talc (100 mg of spores/5 g of talc); after a stay period of 48 hours in a room saturated with moisture, at 21° C., the leaves were treated with the products under examination in a water-acetone solution, containing 20% of acetone (vol./vol.) by spraying both leaf faces.

At the end of the incubation period (14 days), the infection degree was evaluated at sight, by means indexes of a valuation scale ranging from 100 (=sound plant) to 0 (=completely infected plant).

The results are set forth in Table 2 in comparison with a compound of the Belgian patent.

TABLE 2

| Compound No | Dose g/l | Sphaerotheca fuliginea/ cucumber ||| Erysiphe graminis/ wheat || Puccinia graminis/ wheat ||
| --- | --- | --- | --- | --- | --- | --- | --- | --- |
| | | Prevent. Act. | Curat. Act. | Syst. Act. through roots | Prevent. Act. | Curat. Act. | Prevent. Act. | Curat. Act. |
| 1 a + b | 0.5 | 100 | | 100 | | | | 94 |
| (I) + | 0.25 | 100 | | 100 | | | | |
| (II Z) | 0.125 | 100 | | 100 | | | | 60 |
| | 0.06 | 100 | | 100 | | | | |
| 1 b | 0.5 | 100 | | 0 | | | | |
| (II Z) | 0.25 | 100 | | | | | | |
| | 0.125 | 100 | | | | | | |
| | 0.06 | 100 | | | | | | 70 |
| 2 a + b | 0.5 | 100 | | 100 | 100 | | | |
| (I) + | 0.25 | 100 | | 100 | 100 | | | |
| (II Z) | 0.125 | 100 | | 100 | 100 | | | 60 |
| | 0.06 | 100 | | 100 | 100 | | | |
| 3 b | 0.5 | 100 | | 80 | | | | 68 |
| (II Z) | 0.25 | 100 | | | | | | |
| | 0.125 | 100 | | | | | | |
| | 0.06 | 100 | | | | | | |
| 3 a | 0.5 | 100 | | 100 | | | | 100 |
| (I) | 0.25 | 100 | | 100 | | | | — |
| | 0.125 | 100 | | 95 | | | | 80 |
| | 0.06 | | | | | | | — |
| 4 b | 0.5 | 100 | | 50 | | | | 100 |
| (II Z) | 0.25 | 100 | | | | | | 100 |
| | 0.125 | 100 | | 0 | | | | 100 |
| | 0.06 | 100 | | | | | | 90 |
| 4 a | 0.5 | 100 | | 100 | 100 | | | 100 |
| (I) | 0.25 | 100 | | 100 | 100 | | | 100 |
| | 0.125 | 100 | | 100 | 100 | | | 100 |
| | 0.06 | 100 | | 100 | 100 | | | 88 |
| 5 (I) | 0.5 | 100 | | 40 | | | | 100 |
| | 0.25 | 100 | | | | | | |
| | 0.125 | 100 | | | | | | 92 |
| | 0.06 | 100 | | | | | | 50 |
| 6 b | 0.5 | 100 | 100 | 100 | 100 | 100 | 100 | 100 |
| (II Z) | 0.25 | 100 | 100 | 100 | 100 | 100 | 100 | 100 |
| | 0.125 | 100 | 100 | 90 | 100 | 100 | 100 | 100 |
| | 0.06 | 100 | 100 | 80 | 100 | 100 | 92 | 100 |
| 6 a | 0.5 | 100 | | 80 | | | | — |
| (I) | 0.25 | 100 | | | | | | — |
| | 0.125 | 100 | | 60 | | | | 80 |
| | 0.06 | 100 | | | | | | — |
| 6 c | 0.5 | 100 | | 100 | | | | 100 |
| (II E) | 0.25 | 100 | | 100 | | | | 100 |

TABLE 2-continued

| Compound No | Dose g/l | Sphaerotheca fuliginea/ cucumber | | | Erysiphe graminis/ wheat | | Puccinia graminis/ wheat | |
|---|---|---|---|---|---|---|---|---|
| | | Prevent. Act. | Curat. Act. | Syst. Act. through roots | Prevent. Act. | Curat. Act. | Prevent. Act. | Curat. Act. |
| | 0.125 | 100 | | 100 | | | | 100 |
| | 0.06 | 100 | | 100 | | | | 100 |
| 7 (II Z) | 0.5 | 100 | 100 | 100 | | | | 100 |
| | 0.25 | 100 | 100 | 100 | | | | 100 |
| | 0.125 | 100 | 100 | 100 | | | | 100 |
| | 0.06 | 100 | 100 | 70 | | | | 100 |
| 8 (II Z) | 0.5 | 100 | 100 | 100 | | | | 100 |
| | 0.25 | 100 | 100 | | | | | 100 |
| | 0.125 | 100 | 100 | 80 | | | | 100 |
| | 0.06 | 100 | 100 | | | | | 90 |
| 9 (II Z) | 0.5 | 100 | | 85 | | | | 100 |
| | 0.25 | 100 | | | | | | — |
| | 0.125 | 100 | | | | | | 60 |
| | 0.06 | 100 | | | | | | — |
| Ref. * | 0.5 | 100 | 100 | 0 | | | | 0 |
| | 0.25 | 100 | 100 | | | | | |
| | 0.125 | 100 | 100 | | | | | |
| | 0.06 | 100 | 100 | | | | | |

* The compound having formula:

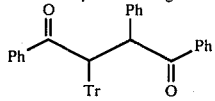

We claim:
1. Compounds having the formula:

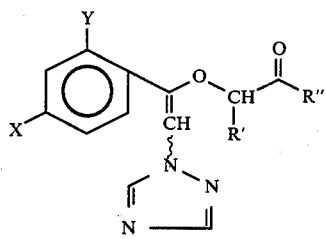

wherein:
R' and R", equal to or different from each other, represent a linear or branched $C_1$-$C_7$ alkyl group; a $C_3$-$C_7$ cycloalkyl group, optionally substituted by $C_1$-$C_4$ alkyl groups; an alkoxyalkyl group having from 1 to 4 carbon atoms both in the alkyl part and in the alkoxyl part;
X represents a halogen atom; a $C_1$-$C_4$ alkyl group; a $C_1$-$C_4$ haloalkyl group; a $C_1$-$C_4$ alkoxy group; or a phenyl group; and
Y represents H or a halogen atom.

2. Compounds according to claim 1, wherein:
R'=R" represent linear or branched $C_1$-$C_7$ alkyl groups,
X=Cl or F; and
Y=H, Cl or F.

3. Compounds according to claim 1, wherein:
R' and R" represent linear or branched $C_1$-$C_7$ alkyl groups, different from each other (R'≠R");
X=Cl or F; and
Y=H, Cl or F.

4. Compounds according to claim 1, wherein:
R'=a $C_1$-$C_4$ alkoxyalkyl group, having 1 to 4 carbon atoms, both in the alkyl part and in the alkoxyl part;
R"=a linear or branched $C_1$-$C_7$ alkyl group;
X=Cl or F; and
Y=H, Cl or F.

5. The compound having the formula:

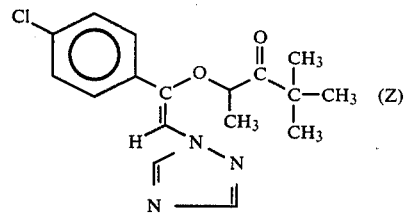

having a melting point of 112°-113° C.

6. The compound having the formula:

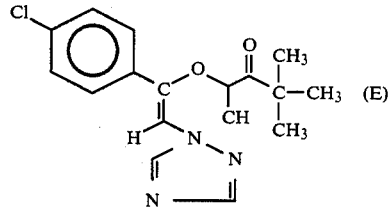

having a melting point of 72°-74° C.

7. The compound having the formula:

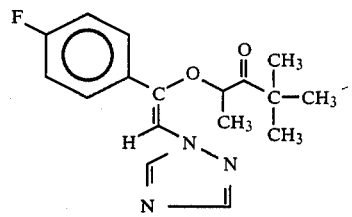

having a melting point of 98°-100° C.

8. A method of fighting fungus infections in useful plants consisting in distributing on the plant, on the seeds or in the surrounding soil, when the fungus infection is foreseen or it is already in progress, an effective amount of a compound according to claim 1, as such or in the form of a suitable composition.

9. Compositions having as active ingredient one or more compounds according to claim 1, together with an inert solid or liquid carrier.

* * * * *

UNITED STATES PATENT AND TRADEMARK OFFICE
CERTIFICATE OF CORRECTION

PATENT NO. : 4,766,139

DATED : August 23, 1988

INVENTOR(S) : COLLE et al.

It is certified that error appears in the above-identified patent and that said Letters Patent is hereby corrected as shown below:

In the heading, please correct the following error:

"[30] Foreign Application Priority Data

Apr. 11, 1984 [IT] Italy ......20484 A/85" to

--[30] Foreign Application Priority Data

Apr. 11, 1984 [IT] Italy.......20484 A/84"--

At column 5, line 35, the formula of the compound on the right, should read as follows:

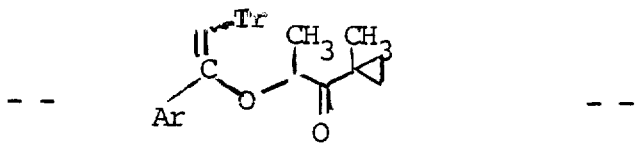

UNITED STATES PATENT AND TRADEMARK OFFICE
CERTIFICATE OF CORRECTION

PATENT NO. : 4,766,139
DATED : August 23, 1988
INVENTOR(S) : COLLE et al.

PAGE 2 of 3

It is certified that error appears in the above-identified patent and that said Letters Patent is hereby corrected as shown below:

At column 5, line 65, in the formula of the compound on the right, should read as follows:

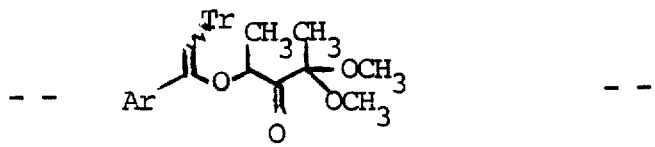

UNITED STATES PATENT AND TRADEMARK OFFICE
CERTIFICATE OF CORRECTION

PATENT NO. : 4,766,139

DATED : August 23, 1988

INVENTOR(S) : COLLE et al.

It is certified that error appears in the above-identified patent and that said Letters Patent is hereby corrected as shown below:

Claim 6, in the formula of the compound should read as follows:

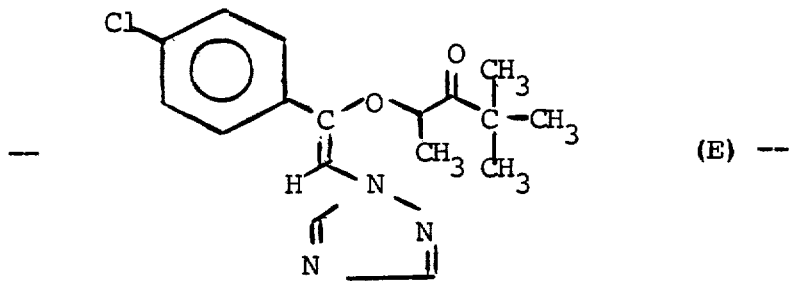

Signed and Sealed this

Seventh Day of November, 1989

Attest:

JEFFREY M. SAMUELS

*Attesting Officer*   Acting Commissioner of Patents and Trademarks